(12) United States Patent
Gagnon

(10) Patent No.: US 6,390,104 B1
(45) Date of Patent: May 21, 2002

(54) DENTURE WASH

(76) Inventor: Steven P. Gagnon, 240 Meeker #7, Delta, CO (US) 81416

( * ) Notice: Subject to any disclaimer, the term of this patent is extended or adjusted under 35 U.S.C. 154(b) by 0 days.

(21) Appl. No.: 09/574,523

(22) Filed: May 19, 2000

(51) Int. Cl.[7] .................................................. B08B 3/10
(52) U.S. Cl. ........................ 134/107; 134/135; 134/199; 134/200; 134/201; 134/176; 134/179
(58) Field of Search ............................ 134/84, 85, 135, 134/172, 198, 199, 200, 201, 174, 176, 179, 107

(56) References Cited

U.S. PATENT DOCUMENTS

| 798,186 | A | * | 8/1905 | Karlss |
| 1,469,625 | A | | 10/1923 | Dodge |
| 1,899,495 | A | * | 2/1933 | Celaya |
| 2,163,862 | A | * | 6/1939 | Wing |
| 2,443,988 | A | * | 6/1948 | Morse |
| 2,669,243 | A | * | 2/1954 | Reynolds et al. |
| 2,896,642 | A | * | 7/1959 | Lilly |
| 2,977,963 | A | * | 4/1961 | Klint |
| 3,009,468 | A | * | 11/1961 | Eberle |
| 3,098,496 | A | * | 7/1963 | Milbourne |
| 3,181,541 | A | * | 5/1965 | Brooking |
| 4,157,922 | A | | 6/1979 | Luik |
| 4,295,730 | A | * | 10/1981 | Fraser |
| 4,336,816 | A | | 6/1982 | Horz et al. |
| 4,509,545 | A | * | 4/1985 | Trotter |
| 4,714,855 | A | * | 12/1987 | Jackson et al. |
| 4,784,167 | A | * | 11/1988 | Thomas et al. |
| 4,922,939 | A | | 5/1990 | Adamezyk |
| 5,143,101 | A | * | 9/1992 | Mor |
| 5,357,993 | A | * | 10/1994 | St. Martin |
| 5,515,877 | A | * | 5/1996 | Dunn, Jr. |
| D372,535 | S | | 8/1996 | Dicianna et al. |
| 5,671,664 | A | * | 9/1997 | Jacobson |
| 5,758,675 | A | * | 6/1998 | Scheyer |
| 5,890,503 | A | * | 4/1999 | Bowen |
| 5,906,216 | A | | 5/1999 | Barlet |
| 6,217,933 | B1 | * | 4/2001 | Edwards et al. |

FOREIGN PATENT DOCUMENTS

| FR | 2738479 | * | 3/1997 |
| FR | 2760350 | * | 9/1998 |
| JP | 10-244233 | * | 9/1998 |
| JP | 11-151256 | * | 6/1999 |

OTHER PUBLICATIONS

European Patent Application 465,285, Jan. 1992.*

* cited by examiner

Primary Examiner—Frankie L. Stinson

(57) ABSTRACT

A denture wash for more thoroughly and easily cleaning dentures. The denture wash includes a lower assembly comprising a bottom wall, four walls, a plurality of nozzles, a first central nozzle, and a pump, a upper unit assembly comprising a lid, four walls, a plurality of nozzles, and a second central nozzle, and a denture holding assembly.

17 Claims, 4 Drawing Sheets

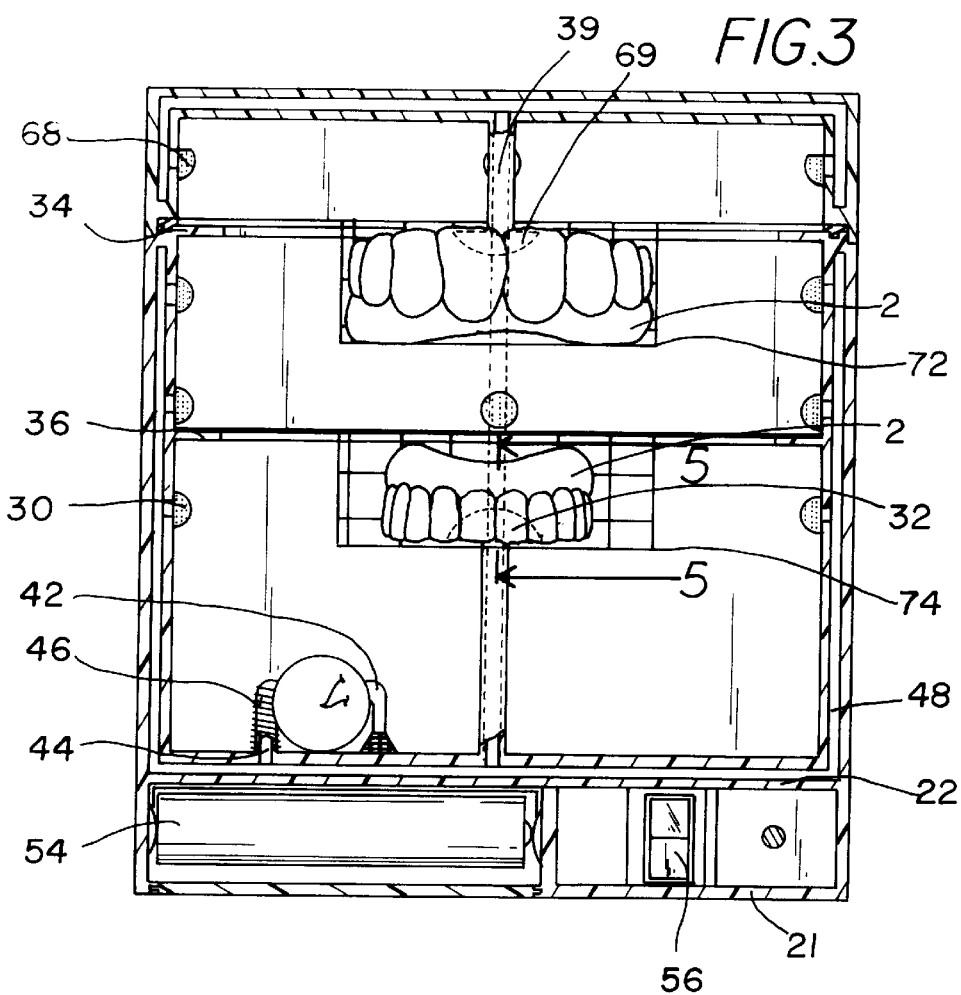
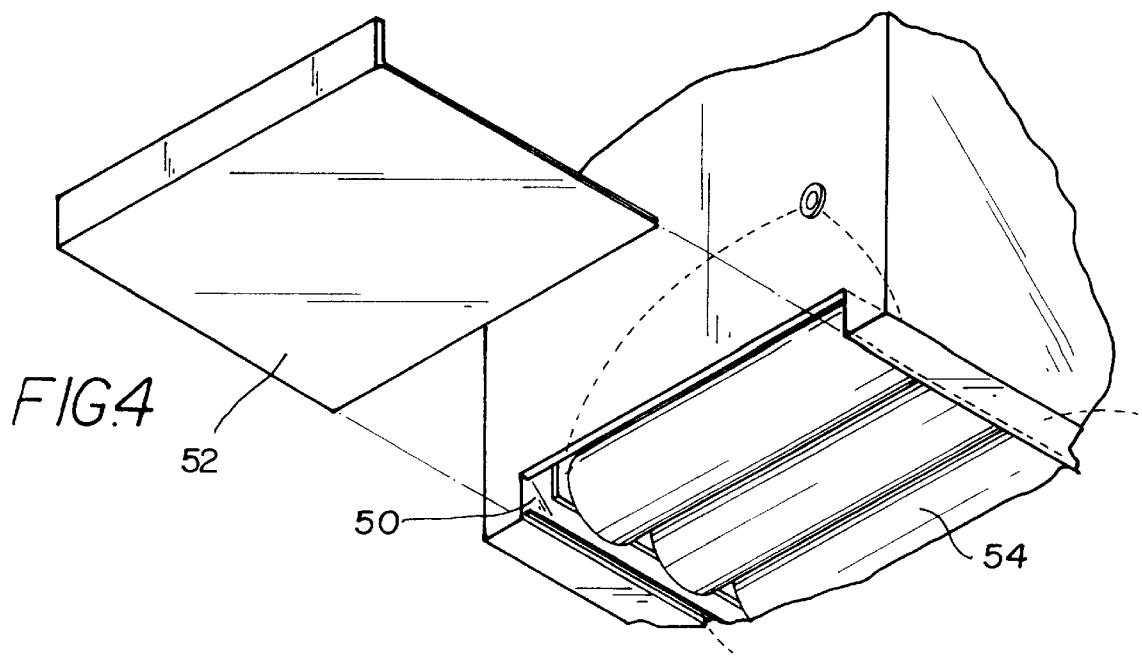

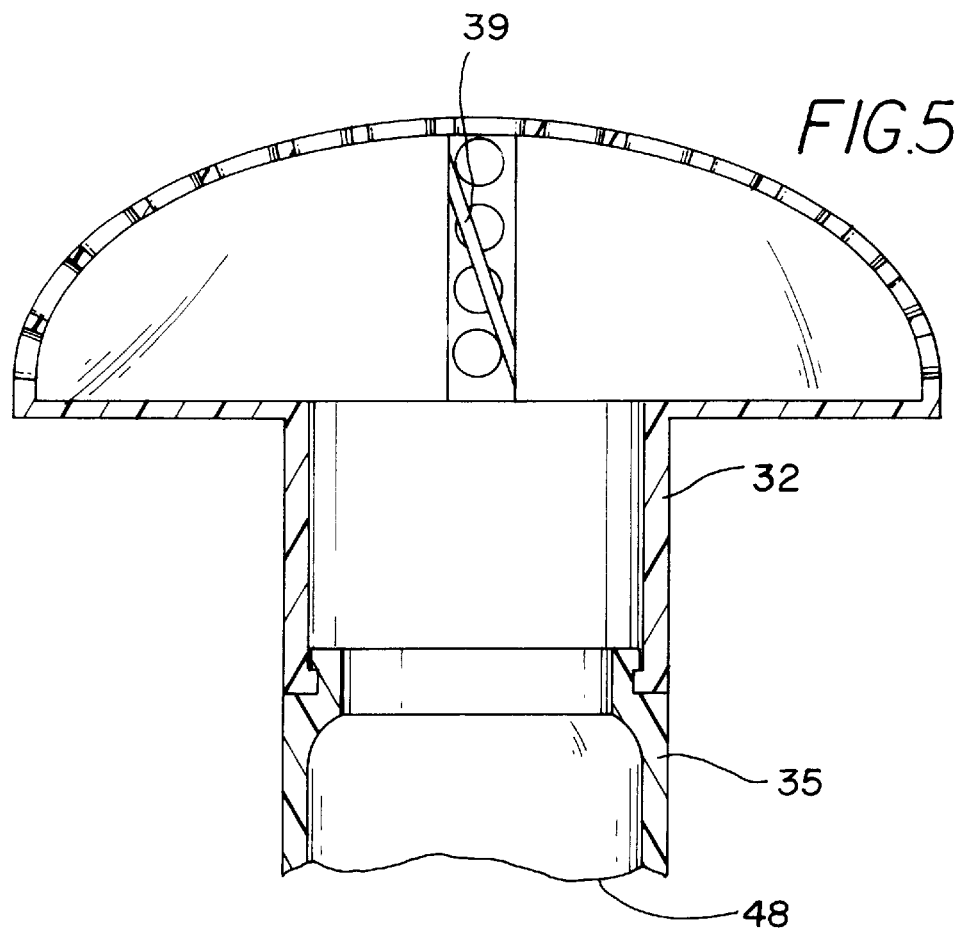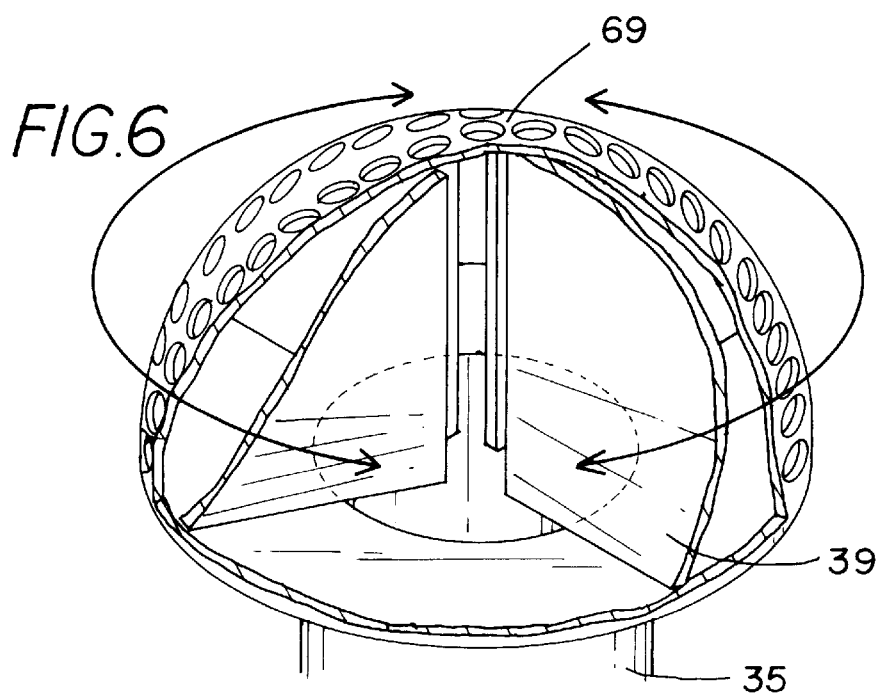

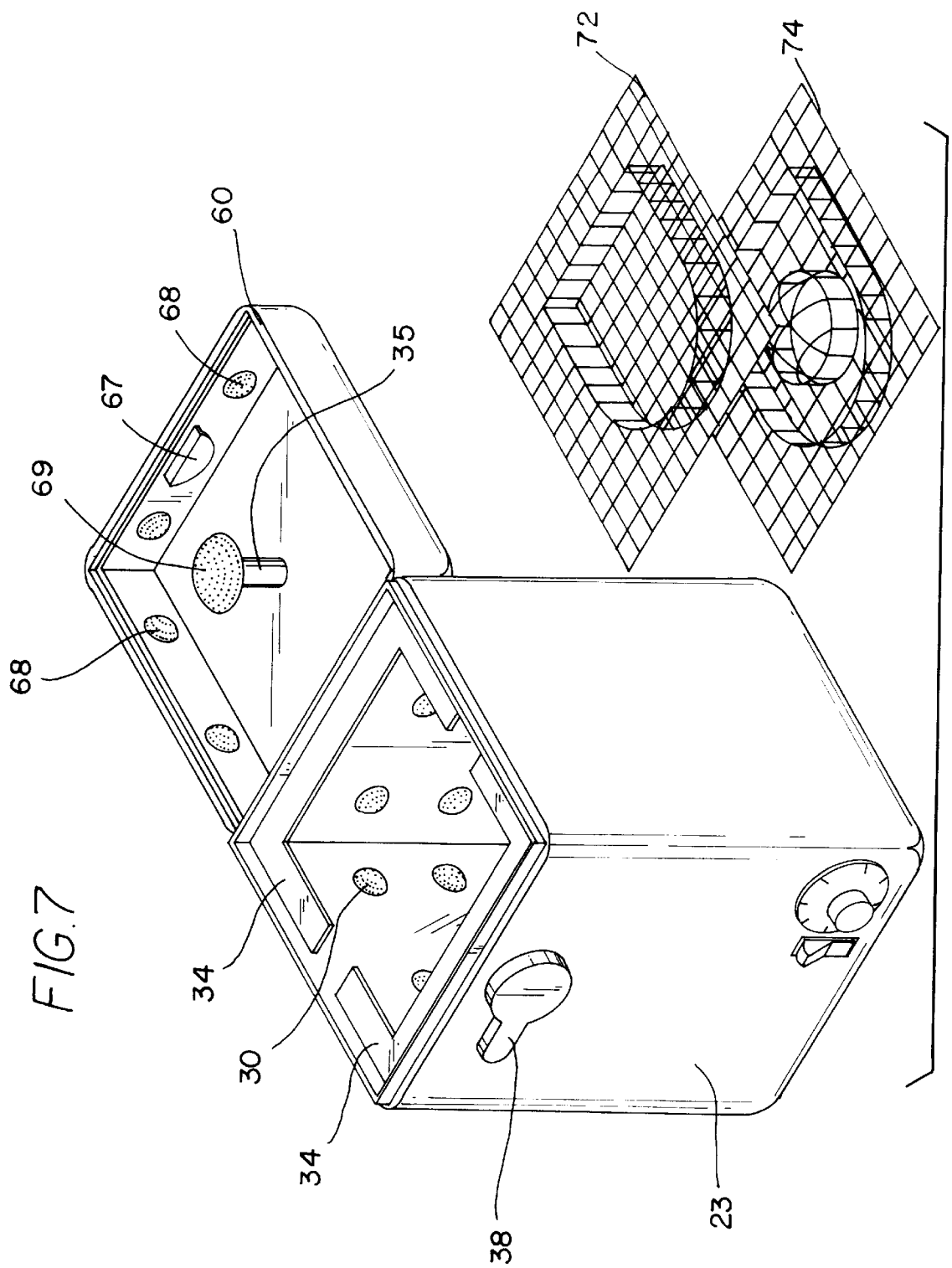

DENTURE WASH

BACKGROUND OF THE INVENTION

1. Field of the Invention

The present invention relates to denture cleaning devices and more particularly pertains to a new denture wash for more thoroughly and easily cleaning dentures.

2. Description of the Prior Art

The use of denture cleaning devices is known in the prior art. More specifically, denture cleaning devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 4,922,939; 4,336,816; 1,469,625; 4,157,922; 5,515,877; and U.S. Pat. No. Des. 372,535.

While these devices fulfill their respective, particular objectives and requirements, the aforementioned patents do not disclose a new denture wash. The inventive device includes a lower assembly comprising a bottom wall, four walls, a plurality of nozzles, a first central nozzle, and a pump; and an upper unit assembly comprising a lid, four walls, a plurality of nozzles, and a second central nozzle; and a denture holding assembly.

In these respects, the denture wash according to the present invention substantially departs from the conventional concepts and designs of the prior art, and in so doing provides an apparatus primarily developed for the purpose of more thoroughly and easily cleaning dentures.

SUMMARY OF THE INVENTION

In view of the foregoing disadvantages inherent in the known types of denture cleaning devices now present in the prior art, the present invention provides a new denture wash construction wherein the same can be utilized for more thoroughly and easily cleaning dentures.

The general purpose of the present invention, which will be described subsequently in greater detail, is to provide a new denture wash apparatus and method which has many of the advantages of the denture cleaning devices mentioned heretofore and many novel features that result in a new denture wash which is not anticipated, rendered obvious, suggested, or even implied by any of the prior art denture cleaning devices, either alone or in any combination thereof.

To attain this, the present invention generally comprises a lower assembly comprising a bottom wall, four walls, a plurality of nozzles, a first central nozzle, and a pump; and an upper unit assembly comprising a lid, four walls, a plurality of nozzles, and a second central nozzle; and a denture holding assembly.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set fourth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new denture wash apparatus and method which has many of the advantages of the denture cleaning devices mentioned heretofore and many novel features that result in a new denture wash which is not anticipated, rendered obvious, suggested, or even implied by any of the prior art denture cleaning devices, either alone or in any combination thereof.

It is another object of the present invention to provide a new denture wash which may be easily and efficiently manufactured and marketed.

It is a further object of the present invention to provide a new denture wash which is of a durable and reliable construction.

An even further object of the present invention is to provide a new denture wash which is susceptible of a low cost of manufacture with regard to both materials and labor, and which accordingly is then susceptible of low prices of sale to the consuming public, thereby making such denture wash economically available to the buying public.

Still yet another object of the present invention is to provide a new denture wash which provides in the apparatuses and methods of the prior art some of the advantages thereof, while simultaneously overcoming some of the disadvantages normally associated therewith.

Still another object of the present invention is to provide a new denture wash for more thoroughly and easily cleaning dentures.

Yet another object of the present invention is to provide a new denture wash which includes a bottom wall, four walls, a plurality of nozzles, a first central nozzle, and a pump; and an upper unit assembly comprising a lid, four walls, a plurality of nozzles, and a second central nozzle; and a denture holding assembly.

Still yet another object of the present invention is to provide a new denture wash that reduces the time necessary to clean and sanitize dentures.

Even still another object of the present invention is to provide a new denture wash that cleans dentures without tablets, cups, or soaking.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a schematic sectional view of the present invention.

FIG. 4 is a schematic perspective view of the lower unit assembly particularly illustrating the battery holding compartment of the present invention.

FIG. 5 is a schematic sectional view along line 5—5 in FIG. 3 of the present invention.

FIG. 6 is a schematic perspective view of one of the nozzles of the present invention with a portion broken away to show interior detail.

FIG. 7 is a schematic perspective view of the present invention with the upper unit assembly in an open condition.

DESCRIPTION OF THE PREFERRED EMBODIMENT

Figure 1:
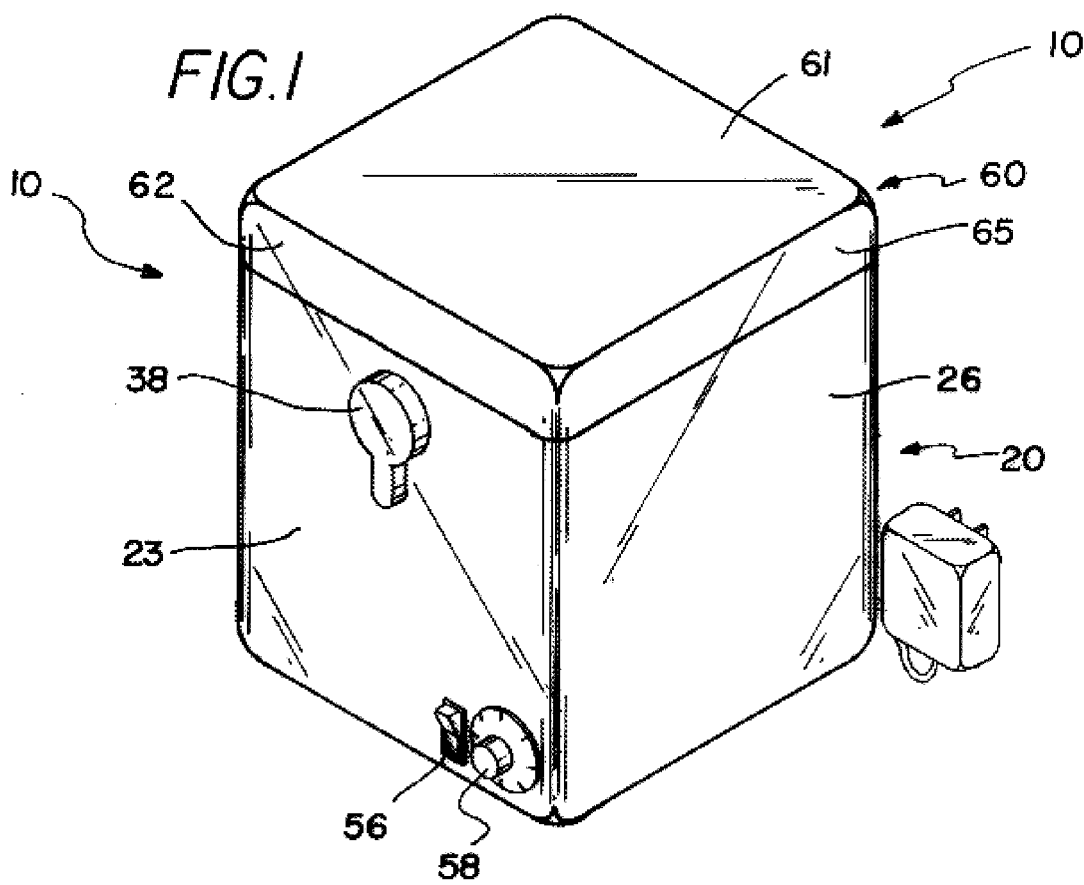
FIG. 1 is a schematic perspective view of a new denture wash according to the present invention.
Figure 2:
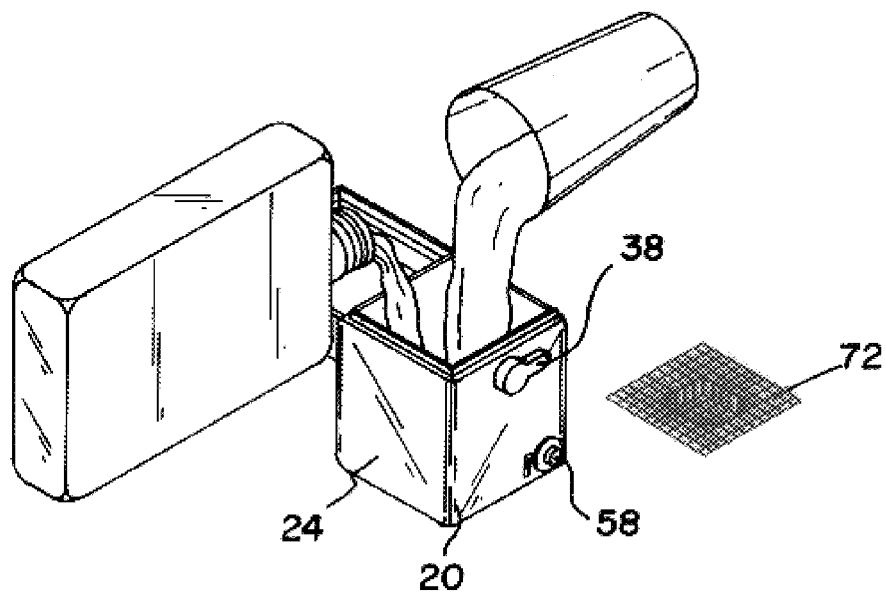
FIG. 2 is a schematic view of elements of the present invention in use.

With reference now to the drawings, and in particular to FIGS. 1 through 7 thereof, a new denture wash embodying the principles and concepts of the present invention and generally designated by the reference numeral 10 will be described.

As best illustrated in FIGS. 1 through 7, the denture wash 10 generally comprises A denture washing system 10 for more thoroughly and easily cleaning dentures 2. The denture washing system 10 comprises a lower unit assembly 20, an upper unit assembly 60, and a denture holding assembly 70. The lower unit assembly 20 is substantially rectangular in configuration, and has a base 21 for resting on a surface. The lower unit assembly comprises a bottom wall 22, a first 23, second 24, third 25 and fourth wall 26, and also includes a plurality of nozzles 30, a first central nozzle 32, a pump 40. The lower unit assembly further includes a first ledge 34, second ledge 36, a latch 38, a battery holding compartment 50, an adapter socket 59, and on/off switch 56, and an adjustable timer 57. The upper unit assembly 60 comprises a lid 61 formed by a first 62, second 63, third 64, and fourth wall 65, and including a flexible conduit connector 66, a latch receiver 67, a plurality of nozzles 68, and a second central nozzle 69. The denture holding assembly 70 comprises a top rack 72 and a bottom rack 74.

The bottom wall 22 of the lower unit assembly 20 may be located parallel to and above the base 21. The bottom wall 22 has an inner surface and an outer surface with a conduit 48 in between.

The first 23, second 24, third 25, and fourth walls 26 of the lower unit assembly each have an inner surface and an outer surface. The walls 23, 24, 25, 26 are coupled adjacent to the bottom wall 22 to define a chamber for holding a cleaning solution. The first 23, second 24, third 25, and fourth walls 26 each have at least one conduit 48 located between the inner surface and the outer surface. Each conduit 48 is coupled to the conduit 48 of the bottom wall 22 and to the nozzles 30 of the respective wall for dispensing the cleaning solution within the chamber.

The plurality of nozzles 30 are located on the inner surface of the first 23, second 24, third 25, and fourth walls 26. The nozzles 30 have a dome shape with a plurality of dispensing holes. The nozzles 30 are coupled to each of the conduits 48 of the first 23, second 24, third 25, and fourth walls 26 for dispensing the cleaning solution.

The first central nozzle 32 is coupled to an elongated stem 35 centrally located on the inner surface of the bottom wall 22. The stem 35 has two opposite ends and a conduit 48 running the length of the stem 35. The stem 35 has one end fixedly coupled to the conduit 48 of the bottom wall 22. The other end of the stem 35 is rotatably coupled to the first central nozzle 32. The first central nozzle 32 has a dome shape with a plurality of holes. The first central nozzle 32 has at least one blade 39 mounted within, at an angle sufficient to rotate the first central nozzle 32 when the cleaning solution comes into contact with the blade 39.

The pump 40 has an inlet tube 42 and an outlet tube 44 for circulating the cleaning solution from the chamber to the conduit 48 of the bottom wall 22. The outlet tube 44 is coupled to the conduit 48 of the bottom wall 22. A heating element 46 is spirally wrapped around the outlet tube 44 for heating the cleaning solution before entering the conduit 48 of the bottom wall 22.

The first ledge 34 and second ledge 36 extend perpendicularly from the inner surface of the first 23, second 24, third 25, and fourth walls 26. The first ledge 34 and second ledge 36 are laterally spaced with the second ledge 36 being located below the first ledge 34. The first ledge 34 has an opening on two of the oppositely facing walls.

The latch 38 is rotatably mounted to the outer surface of the first wall 23. The latch 38 has an extent for being grasped by the user and rotated between a locked and unlocked position.

The battery holding compartment 50 is located between the base 21 and the outer surface of the bottom wall 22 for securing at least one battery 54. The battery holding compartment 50 has a battery door 52 which is removably coupled to the base 21 for allowing access to the battery holding compartment 50.

The adapter socket 59 is located on the outer surface of the third wall 25. The adapter socket 59 is designed to receive a recharging unit plug. The adapter socket 59 is coupled to the battery holding compartment 50 by insulated wire 55 for recharging the battery 54.

The on/off switch 56 is located between the base 21 and the outer surface of the bottom wall 22. The on/off switch 56 protrudes through an opening in the first wall 23 for easy activation by the user. The on/off switch 56 is coupled to the battery 54 by insulated wire 55.

The adjustable timer 57 is located between the base 21 and the outer surface of the bottom wall 22. The adjustable timer 57 has an adjustment knob 58 located on the outer surface of the first wall 23; and is coupled to the adjustable timer 57 by way of a hole through the first wall 23. The adjustable timer 57 is coupled to the on/off switch 56, the pump 40, and the heating element 46 by insulated wire 55.

The upper unit assembly 60 is pivotally coupled to the lower unit assembly 20. The upper unit assembly 60 comprises a lid 61, a first 62, second 63, third 64, and fourth wall 65, a flexible conduit connector 66, a latch receiver 67, a plurality of nozzles 68, and a second central nozzle 69.

The lid 61 is substantially rectangular in configuration. The lid 61 has an inner surface and an outer surface with a conduit 48 between the two surfaces.

The first 62, second 63, third 64, and fourth walls 65 each have an inner surface and an outer surface, with at least one conduit 48 located between the surfaces of each wall. Each of the walls is coupled to the lid 61, and the conduit 48 located between the inner and outer surface for each wall is connected to the conduit 48 in between the inner and outer surface of the lid 61. The third wall 64 of the upper unit assembly 60 is pivotally coupled to the third wall 25 of the lower unit assembly 20.

The flexible conduit connector 66 is coupled to the conduit 48 of the third wall 25 of the lower unit assembly 20 and to the conduit 48 of the third wall 64 of the upper unit assembly 60 for supplying the cleaning solution to the upper unit assembly 60.

The latch receiver 67 is located on the inner surface of the first wall 62 for securely retaining the upper unit assembly 60 in a closed position when the latch 38 is rotated into the lock position.

The plurality of nozzles 68 are located on the inner surface of the first 62, second 63, third 64, and fourth walls 65. The nozzles 68 each have a semi-dome shape with a plurality of dispensing holes facing away from the lid 61. The nozzles 68 are coupled to each of the conduits 48 of the respective wall for dispensing the cleaning solution within the chamber.

The second central nozzle 69 is coupled to an elongated stem 35 centrally located on the inner surface of the lid 61. The stem 35 has two ends and a conduit 48 running the length of the stem 35. One end of the stem 35 is fixedly coupled to the conduit 48 of the lid 61. The second end of the stem 35 is rotatably coupled to the second central nozzle 69. The second central nozzle 69 has a dome shape with a plurality of holes. The second central nozzle 69 has at least one blade 39 mounted internally with an angle sufficient enough to rotate the second central nozzle 69 when the cleaning solution comes into contact with the blade 39.

The denture holding assembly 70 retains the dentures 2 in a secure position within the lower unit assembly 20. The dentures 2 have a gum side and a tooth side. The denture holding assembly 70 comprises a top rack 72 and a bottom rack 74.

The top rack 72 has a substantially rectangular configuration and is made of a mesh sheet. The top rack 72 has a detent section that is larger in size than the denture 2. The openings in the mesh sheet are large enough to allow the cleaning solution to pass easily through the sheet. The top rack 72 is removably coupled to the first ledge 34 with the detent section in a downward position. The denture 2 is placed in the detent with the tooth side in an upward position and the gum side in contact with the detent.

The bottom rack 74 has a substantially rectangular configuration and is made of a mesh sheet. The bottom rack 74 has a detent section that is larger than the size of the denture 2. The detent section has an upwardly extending portion located in the center of the detent section of the bottom rack 74. The upwardly extending portion is larger in size than the first central nozzle 32. The openings in the mesh sheet are large enough to allow the cleaning solution to pass easily through the mesh sheet. The bottom rack 74 is removably coupled to the second ledge 36 by way of the openings of the first ledge 34. The detent section of the bottom rack 74 is placed in a downward position and the denture 2 is place in the detent over the upwardly extending portion with the gum side in an upward position and the tooth side in contact with the detent.

In use, the latch on the denture wash will be moved to the unlock position. The upper unit assembly will then be pivoted to the open position with respect to the lower unit assembly. A denture will be placed on the bottom rack, which will then be placed on the second ledge inside the denture wash. A second denture may then be positioned on the top rack, which is then positioned on the first ledge. A cleaning solution is then placed in the chamber of the denture wash. The upper unit assembly is then pivoted to the closed position with respect to the lower unit assembly. The latch is rotated to the lock position. The user will then set the timer adjustment and toggle the on/off switch. After the time set on the adjustable timer has elapsed, the user may then remove the dentures in a similar manner as described above.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A denture washing system for more thoroughly and easily cleaning dentures, the denture washing system comprising:
   a lower unit assembly comprising:
      a base for resting on a surface;
      a bottom wall located parallel and above the base, the bottom wall having an inner surface and an outer surface;
      a first, second, third and fourth wall each having an inner surface and an outer surface, the walls being coupled to the bottom wall to define a chamber for holding a cleaning solution therein;
      a plurality of nozzles located on the inner surfaces of the first, second, third and fourth walls;
      a first central nozzle coupled to an elongated stem extending upwardly from the inner surface of the bottom wall, the stem having opposite ends and a conduit running the length of the stem, the stem having one end coupled to the inner surface of the bottom wall and the other end of the stem being rotatably coupled to the first central nozzle;
      a pump for circulating the cleaning solution from the chamber to the nozzles;
   an upper unit assembly pivotally coupled to the lower unit assembly, the upper unit assembly comprising:
      a lid having an inner surface;

a first, second, third and fourth wall each having an inner surface and an outer surface, the walls being coupled to the lid, the third wall of the upper unit assembly being pivotally coupled to the third wall of the lower unit assembly;

a plurality of nozzles located on the inner surface of the first, second, third and fourth walls of the upper unit assembly; and a second central nozzle coupled to an elongated stem centrally located on the inner surface of the lid;

a denture holding assembly for retaining dentures having a gum side and a tooth side in a secure position in the lower unit assembly, the denture holding assembly comprising:

a top rack formed of a mesh sheet, the top rack having a detent section that is larger than the size of the denture; and a bottom rack formed of a mesh sheet, the bottom rack having a detent section that is larger than the size of the denture, the detent section having an upwardly extending portion located in the center of the detent section of the bottom rack and is larger than the first central nozzle of the lower unit assembly.

2. The denture washing system of claim 1 wherein the first, second, third and fourth walls each have at least one conduit located between the inner surface and the outer surface of each of the walls, and the conduit of each wall being fluidly connected to a conduit in the bottom wall, the conduit of each of the walls being fluidly connected to the nozzle of the respective wall.

3. The denture washing system of claim 1 wherein the nozzles each have a dome shape with a plurality of fluid dispensing holes.

4. The denture washing system of claim 1 wherein the first central nozzle has a dome shape with a plurality of holes, the first central nozzle having at least one blade mounted in the first central nozzle at an angle sufficient enough to rotate the first central nozzle when the cleaning solution comes into contact with the blade.

5. The denture washing system of claim 1 wherein the pump has an inlet and an outlet tube, the outlet tube being fluidly coupled to the conduit of the bottom wall.

6. The denture washing system of claim 1 wherein the pump has an outlet tube with a heating element wrapped around the outlet tube for heating of the cleaning solution before entering the nozzles.

7. The denture washing system of claim 1 wherein a first ledge and a second ledge extend perpendicularly from the inner surface of the first, second, third and fourth walls, the first ledge and second ledge being spaced with the second ledge being located below the first ledge, the first ledge having an opening on two of oppositely facing walls.

8. The denture washing system of claim 1 wherein additionally comprising a latch rotatably mounted to one of the unit assemblies and a latch receiver mounted on the other of the unit assemblies, the latch having an extent for being grasped by a user and rotated between a locked and unlocked position, and the latch receiver for receiving the latch when the latch is rotated into the lock position for securely retaining the upper unit assembly in a closed position.

9. The denture washing system of claim 1 additionally comprising a battery holding compartment located between the base and the bottom wall for securing at least one battery.

10. The denture washing system of claim 1 wherein the battery holding compartment has a battery door removably coupled to the base for allowing access to the battery compartment.

11. The denture washing system of claim 1 additionally comprising an adapter socket located on the outer surface of the lower unit assembly and adapted to receive a recharging unit plug.

12. The denture washing system of claim 1 wherein an on/off switch is located on the lower unit assembly.

13. The denture washing system of claim 1 wherein an adjustable timer is located on the lower unit assembly with an adjustment knob located on the outer surface of the first wall.

14. The denture washing system of claim 1 wherein the stem of the lid has an end rotatably coupled to the second central nozzle, the second central nozzle having a dome shape with a plurality of holes, the second central nozzle having at least one blade mounted within the second central nozzle at an angle sufficient enough to rotate the second central nozzle when the cleaning solution comes into contact with the blade.

15. The denture washing system of claim 1 wherein the top rack is removably coupled to the first ledge with the detent section in a downward position and the denture placed in the detent with the tooth side in an upward position and the gum side in contact with the detent.

16. The denture washing system of claim 1 wherein the bottom rack is removably coupled to the second ledge by way of the openings of the first ledge with the detent section in a downward position and a denture is positionable in the detent over the upwardly extending portion with the gum side in an upward position and the tooth side in contact with the detent.

17. A denture washing system for more thoroughly and easily cleaning dentures, the denture washing system comprising:

a lower unit assembly having a substantially rectangular configuration with a base for resting on a surface, the lower unit assembly comprising:

a bottom wall located parallel and above the base, the bottom wall having an inner surface and an outer surface with a conduit therebetween;

a first, second, third and fourth wall having an inner surface and an outer surface, the walls being coupled adjacent to the bottom wall to define a chamber for holding a cleaning solution therein, the first, second, third and fourth walls each having at least one conduit located between the inner surface and the outer surface and each conduit being coupled to the conduit of the bottom wall;

a plurality of nozzles located on the inner surface of the first, second, third and fourth walls, the nozzles having a dome shape with a plurality of dispensing holes, the nozzles being coupled to each of the conduits of the first, second, third and fourth walls for dispensing the cleaning solution within the chamber;

a first central nozzle coupled to an elongated stem centrally located on inner surface of the bottom wall, the stem having opposite ends and a conduit running the length of the stem, the stem having one end fixedly coupled to the conduit of the bottom wall and the other end rotatably coupled to the first central nozzle, the first central nozzle having a dome shape with a plurality of holes, the first central nozzle having at least one blade mounted within the first central nozzle at an angle sufficient enough to rotate the first central nozzle when the cleaning solution comes into contact with the blade;

a pump having an inlet tube and an outlet tube for circulating the cleaning solution from the chamber to the conduit of the bottom wall, the inlet tube having a slotted tapered inlet port coupled to the inner surface of the bottom wall, the outlet tube coupled to the conduit of the bottom wall and having a heating element spirally wrapped around the outlet tube for heating of the cleaning solution before entering the conduit of the bottom wall;

a firs ledge and a second ledge perpendicularly extending from the inner surface of the first, second, third and fourth walls, the first ledge and second ledge being laterally spaced with the second ledge located below the first ledge, the first ledge having an opening on two of oppositely facing walls;

a latch rotatably mounted to the outer surface of the first wall, the latch having an extent for being grasped by a user and rotated between a locked and unlocked position;

a battery holding compartment located between the base and the outer surface of the bottom wall for securing at least one battery, the battery holding compartment having a battery door removably coupled to the base for allowing access to the battery compartment;

an adapter socket located on the outer surface of the third wall adapted to receive a recharging unit plug, the adapter socket being coupled to the battery compartment by an insulated wire for recharging of the battery;

an on/off switch located between the base and the outer surface of the bottom wall and protruding through an opening in the first wall for easy activation of the user, the on/off switch being coupled to the battery by an insulated wire; and an adjustable timer located between the base and the outer surface of the bottom wall, the adjustable time having an adjustment knob located on the outer surface of the first wall and coupled to the adjustable timer by way of a hole through the first wall, the adjustable timer being coupled to the on/off switch, the pump and the heating element by an insulated wire;

an upper unit assembly pivotally coupled to the lower unit assembly, the upper unit assembly comprising:

a lid having a substantially rectangular configuration, the lid having an inner surface and an outer surface with a conduit therebetween;

a first, second, third and fourth wall having an inner surface and an outer surface, the walls being coupled adjacent to the lid, the first, second, third and fourth walls each having at least one conduit located between the inner surface and the outer surface and each conduit being coupled to the conduit of the lid, the third wall of the upper unit assembly being pivotally coupled to the third wall of the lower unit assembly;

a flexible conduit connector being coupled to the conduit of the third wall of the lower unit assembly and to the conduit of the third wall of the upper unit assembly for supplying the cleaning solution to the upper unit assembly;

a latch receiver located on the inner surface of the first wall for securely retaining the upper unit assembly in a closed position when the latch is rotated into the lock position;

a plurality of nozzles located on the inner surface of the first, second, third and fourth walls of the upper unit assembly, the nozzles having a semi-dome shape with a plurality of dispensing holes facing away from the lid, the nozzles being coupled to each of the conduits of the first, second, third and fourth walls of the upper unit assembly for dispensing the cleaning solution within the chamber; and a second central nozzle coupled to an elongated stem centrally located on the inner surface of the lid, the stem having opposite ends and a conduit running the length of the stem, the stem having one end fixedly coupled to the conduit of the lid and the other end rotatably coupled to the second central nozzle, the second central nozzle having a dome shape with a plurality of holes, the second central nozzle having at least one blade mounted within the second central nozzle at an angle sufficient enough to rotate the second central nozzle when the cleaning solution comes into contact with the blade;

a denture holding assembly for retaining dentures having a gum side and a tooth side in a secure position within the lower unit assembly, the denture holding assembly comprising:

a top rack having a substantially rectangular configuration made of a mesh sheet, the top rack having a detent section that is larger than the size of the denture, the openings in the mesh sheet are large enough to allow the cleaning solution to easily pass through, the top rack being removably coupled to the first ledge with the detent section in a downward position and the denture placed in the detent with the tooth side in an upward position and the gum side in contact with the detent; and a bottom rack having a substantially rectangular configuration made of a mesh sheet, the bottom rack having a detent section that is larger than the size of the denture, a detent section having an upwardly extending portion located in the center of the detent section of the bottom rack and is larger than the first central nozzle of the lower unit assembly, the openings in the mesh sheet are large enough to allow the cleaning solution to easily pass through, the bottom rack being removably coupled to the second ledge by way of the openings of the first ledge with the detent section in a downward position and the denture placed in the detent over the upwardly extending portion with the gum side in an upward position and the tooth side in contact with the detent.

* * * * *